United States Patent [19]

Ito et al.

[11] Patent Number: 5,281,662
[45] Date of Patent: Jan. 25, 1994

[54] ANTHRAQUINONE DYE TREATED MATERIALS

[75] Inventors: Ralph K. Ito, San Juan Capistrano, Calif.; Frank W. LoGerfo, Belmont, Mass.

[73] Assignee: New England Deaconess Hospital Corporation, Boston, Mass.

[21] Appl. No.: 719,031

[22] Filed: Jun. 21, 1991

Related U.S. Application Data

[63] Continuation-in-part of Ser. No. 592,580, Oct. 4, 1990, abandoned, which is a continuation-in-part of Ser. No. 382,411, Jul. 24, 1989, Pat. No. 5,126,140, which is a continuation-in-part of Ser. No. 227,728, Aug. 3, 1988, Pat. No. 5,019,393.

[51] Int. Cl.$^5$ .................. C08G 63/91; C07K 17/02
[52] U.S. Cl. .................. 525/54.1; 525/54.11; 525/383; 525/420; 525/437; 525/453; 525/418; 530/402; 8/643; 8/569
[58] Field of Search .................. 530/810-817, 530/402, 391.9; 436/85, 86, 800, 8; 8/639, 643, 569; 525/54.1, 54.11, 383, 420, 437, 453, 418

[56] References Cited

U.S. PATENT DOCUMENTS

| | | | |
|---|---|---|---|
| 3,719,488 | 3/1973 | Locatell | 430/422 |
| 3,754,856 | 8/1973 | Johnson | 524/131 |
| 3,847,656 | 11/1974 | Baumann | 428/461 |
| 4,116,898 | 9/1978 | Dudley et al. | 260/17.4 |
| 4,166,105 | 8/1979 | Hirschfield | 530/815 |
| 4,264,326 | 4/1981 | Rau | 8/662 |
| 4,273,873 | 6/1981 | Sugitachi et al. | 435/180 |
| 4,290,770 | 9/1981 | Rau | 8/662 |
| 4,309,181 | 1/1982 | Rau | 8/636 |
| 4,378,224 | 3/1983 | Nimni | 623/11 |
| 4,378,803 | 4/1983 | Takagi et al. | 604/280 |
| 4,447,562 | 5/1984 | Ivani | 523/105 |
| 4,448,889 | 5/1984 | Neri et al. | 436/8 |
| 4,521,564 | 6/1985 | Solomon et al. | 525/54.1 |
| 4,534,971 | 8/1985 | Fisher | 530/853 |
| 4,563,485 | 1/1986 | Fox, Jr. et al. | 523/113 |
| 4,594,407 | 6/1986 | Nyilas et al. | 528/272 |
| 4,600,652 | 7/1986 | Solomon et al. | 428/423.3 |
| 4,720,512 | 1/1988 | Hu et al. | 523/112 |
| 4,828,561 | 5/1989 | Woodroof | 623/8 |
| 4,994,355 | 2/1991 | Dickerson et al. | 430/966 |

FOREIGN PATENT DOCUMENTS

| | | |
|---|---|---|
| 0039670 | 12/1970 | Japan. |
| 61-82760 | 4/1986 | Japan. |
| 2006170 | 1/1987 | Japan. |
| 2082359 | 4/1987 | Japan. |
| 7900638 | 9/1979 | PCT Int'l Appl. |
| 2164343 | 3/1986 | United Kingdom. |

OTHER PUBLICATIONS

Falb et al (1971) Federation Proceedings 30:1688-1691.
Kusserow et al. (1971) Trans. Amer. Soc. Artif. Organs XVII:1-5.
Salyuer et al. (1971) J. Biomed. Mater. Res. Symposium 1:105-127.
Stewart (1977) J. Thoracic and Cardiovasc. Surg. 73:801-803.
Lindon et al. (1978) J. Lab. Clin. Med. 91:47-59.
Sitges-Serra et al. (1980) Surg., Gynecol. & Obstet. 151:481-483.
Kottke-Marchant et al. (1985) pp. 842-848.
Lindon et al. (1985) J. Lab. Clin. Med. 105:219-226.
Joseph (1986) in Introductory Textile Science, Fifth Edition "Dyestuffs and Their Application" #28, pp. 320-327.
NIH Publication No. 85-2185 (not available).
Boffa et al. (1987) J. Histochem and Cytochem. 35:1267-1276.
Clagett (1987) in Hemostasis & Thrombosis, Basic Principles & Clinical Practice (Colman et al., eds) J. B. Lippincott Co., Phila., Pa, pp. 1348-1365.
Salzman et al. (1987) in Hemostasis & Thrombosis, Basic Principles & Clin. Pract. (Colman et al., eds ) J. B. Lippincott Co, Phila, Pa, pp. 1335-1345.
Chandy et al. (1988) Artif. Organs 12:143-151.
Wood (1988) Brit. J. Clin. Practice 42:469-472.

Primary Examiner—Thurman K. Page
Assistant Examiner—G. S. Kishore
Attorney, Agent, or Firm—Lahive & Cockfield

[57] ABSTRACT

Disclosed is a treated material including a base material such as an extrudate, a woven fabric, or unwoven fibers, a disperse dye-type molecule such as a dye or antibiotic dispersed within and non-covalently adhered to the base material, and a molecule-of-interest immobilized on the base material by way of a reactive group on the disperse dye-type molecule. Also disclosed are methods of producing the treated material.

7 Claims, 4 Drawing Sheets

- REACTIVE GROUP
- ⟿ CROSS-LINKING REAGENT

ANTHRAQUINONE DYE TREATED MATERIALS

CROSS-REFERENCE TO RELATED APPLICATIONS

This application is a continuation-in-part of applicants' copending application Ser. No. 592,580, filed Oct. 4, 1990, now abandoned which is a continuation-in-part of applicants' copending patent application Ser. No. 382,411, filed Jul. 24, 1989, now U.S. Pat. No. 5,126,140 which is a continuation-in-part of applicants' copending application Ser. No. 227,728, filed Aug. 3, 1988, now U.S. Pat. No. 5,019,393.

BACKGROUND OF THE INVENTION

The technical field of the present invention is the treatment of natural and artificial materials, and more specifically involves the use of dyes and antibiotics as binding agents for the adherence of preselected molecules to surfaces of natural or artificial materials useful in medical prostheses and in the fabric industry.

The use of artificial or processed natural materials in medical devices and prostheses implanted in the body, or placed in contact with body components, or placed in contact with medicants to be introduced into the body, often poses problems such as, for example, infection in the presence of prosthetic materials, or lack of long term thromboresistance. Thus, the surfaces of medical devices have been treated in an effort to enable or enhance their proper functioning. For example, implantable vascular prostheses made of artificial materials have been treated with biologically active molecules having thrombolytic, anticoagulating, thrombogenesis-inhibiting, and/or platelet inhibiting abilities so as to improve on their thromboresistance (see, e.g., Salzman et al. (1987) in *Hemostasis and Thrombosis: Basic Principles and Clinical Practice*. 2nd Ed., (Colman et al., eds., Lippincott Co., Phila., Pa., pp. 1,335-1,347; Kusserow et al. (1971) Trans. Am. Soc. Artif. Intern. Organs 17:1); and Salyer et al. (1971) *Medical Applications of Plastics*, Biomed. Materials Res. Sym. Gregor, ed.) No. 1 pp. 105).

The attachment of biologically active molecules to artificial substances has proven in many instances to be difficult. For example, the attachment of various thrombogenesis inhibitors directly to solid surfaces in many instances does not result in a stable adherence or long term blood compatibility. Furthermore, the biological activity of the molecule may be compromised by virtue of the mode of attachment.

Therefore, what is needed are new or improved methods of adhering molecules of interest to material surfaces which result in a stable linkage and little loss of activity.

One method of improving on the longevity and effectivity of the linkage is to bind the biologically active molecule to a base coat layer on the material surface, where the base coat layer includes a component having multiple attachment sites available to the biologically active molecule (see U.S. Pat. Nos. 5,019,393 and 5,126,140). By way of example, the base coat layer may be adhered to a synthetic material surface either before or after a thrombogenesis inhibitor is linked to the base coat.

The attachment of other molecules to the surfaces of artificial and natural materials, such as extruded or fibrous substances, is also of general interest. For example, materials treated with antibiotics, growth factors, or cytokines would have many uses in the fields of medicine and basic research.

Alternatively, the treatment of woven fabrics with molecules that impart color, or dyes, is useful to the textile industry. A dye is a compound that can be fixed on a substance in a more or less permanent state and that evokes the visual sensation of a specific color or hue.

In the textile industry it is often the dye, itself, which imparts the desired characteristic, i.e., color, to the fabric. While direct attachment of the dye may be useful, it is often desirable to impart other and/or additional characteristics to the fabric which are not directly provided by the application of known dyes. Such characteristics may include sheen, fluorescence, sparkle, hydrophobicity, an hydrophilicity.

Accordingly, it is an object of the present invention to provide a method of stably adhering molecules of interest to natural and synthetic materials such as extrudates, woven fabrics, and other materials.

Another object of the invention is to provide a treated material to which any number of molecules-of-interest can be stably adhered.

Yet another object is to provide biocompatible synthetic or natural materials useful for implantable and extracorporeal devices or for extracorporeal devices in contact with body tissues or fluids.

Still another object is to provide a molecule-of-interest stably adhered to a fixed support.

These and other objects of the invention will be apparent from the description, drawing, and claims that follow.

SUMMARY OF THE INVENTION

Materials and methods are disclosed herein for the provision of synthetic and natural substances treated with dyes and related molecules to which preselected molecules-of-interest can be stably bound. Such treated substances are useful, for example, as a component of an implantable or extracorporeal device in contact with body tissues or fluids, or as a fabric employed in the textile industry.

It has been discovered that a class of dyes, the disperse dyes, can be used as a means of stably linking a molecule-of-interest to a natural or synthetic base material. A "disperse dye" is a compound that evokes the visual sensation of a specific color or hue, and which can be fixed on a material in a more or less permanent state by absorption into the fibers with no actual chemical reaction occurring between the dye and the fiber. Disperse dyes originally known as acetate dyes include azo-compounds that are mainly monoazo, such as Disperse Blue 11, or diazo, such as Disperse Orange 15, and anthraquinone dyes, such as Disperse Blue 1, 9, 19, 26, Disperse Violet 1 4, 8, Disperse Red 4, 11, 15, 60, Disperse Orange 11, and alizarine, a chelating dye.

As used herein, the term "disperse dyes" also includes substances that are sufficiently duplicative of the structure of acetate dyes such that those substances diffuse into and adhere to a material in substantially the same manner as does an acetate dye. Included are methylene blue and gentian violet.

It has also been discovered that antibiotics such as those having a quinolone structure (e.g., ciprofloxacin), because of their structural similarities to disperse dyes, can be used to treat synthetic and natural materials in a similar manner. Treatment with ciprofloxacin imparts infection resistance to the material, and makes available various reactive groups for binding molecules-of-interest. In addition, treatment with dyes such as methylene blue and gentian violet also results in the impartation of antiseptic properties.

Disperse dyes and various quinolone antibiotics, such as ciprofloxacin, are collectively referred to herein as "disperse dye-type molecules" or "dye-type molecules".

A "molecule-of-interest" or "MOI" is a molecule that imparts a preselected characteristic to the material, and has the capacity to be adhered via chemical linkage to a reactive group on the dye without substantial loss of activity. Preferable MOIs include peptides and proteins such as enzymes, hormones, growth factors, cytokines, and other molecules including antibiotics, glycoproteins, lipoproteins, dyes, hydrogels, synthetic polymers, glycosaminoglycans, metals, and molecules which impart hydrophobicity, hydrophilicity, sparkle, or sheen.

A base material can be given various preselected characteristics by treatment with a disperse dye-type molecule, followed by the linkage of a specific MOI to that dye in such a way that linkage does not compromise the desired activity of the MOI. By way of example, the preselected characteristic may be thrombogenesis inhibition or infection resistance.

Base materials contemplated by the present invention include extrudates, woven fabrics, and unwoven fabrics. Natural or synthetic materials contemplated by the instant invention are preferably polymers such as polyethylene terphthalate, nylon, polyurethane, collagen, polyglycolic acid, polytetrafluoroethylene, and mixtures thereof. One particularly preferred polymeric material comprises polyethylene terphthalate. Other synthetic materials such as acetate, triacetate, acrylic, aramid, modacrylic, olefin, tetrafluoroethylene, polyester, and saran are also useful.

The disperse dye-type molecule includes disperse dyes and any other dyes having a structure sufficiently duplicative of a disperse dye such that at least a portion of these molecules is able to disperse into the material and adhere more or less permanently without covalent linkage thereto. On the molecular level, these dyes are able to enter the intermolecular interstices of the material, whether it be an extrudate, a compress of unwoven fibers, or a woven or knitted fabric.

In preferred aspects of the invention, the disperse dye-type molecules are anthraquinone dyes, azo dyes, or antibiotics. Preferred anthraquinone dyes are selected from the group consisting of Disperse Blue 1, 9, 19, 26, Disperse Red 4, 11, 15, 60, Disperse Violet 1, 4, 8, Disperse Orange 11, and alizarine. Preferred azo dyes include Disperse Blue 11 and Disperse Orange 15. Other preferred dyes with antibacteria characteristics include gentian violet and methylene blue. A particularly preferred quinolone antibiotic is ciprofloxacin and active analogs and fragments thereof.

In accordance with one aspect of the invention, the MOI is immobilized on the base material via a disperse dye-type molecule, at least a portion of which is dispersed within and non-covalently adhered to least one surface of the base material. The disperse dye-type molecule contains a reactive group, such as an amino, sulfhydryl, carboxyl, aldehyde, or ketone group, or a reactive C—H bond, that is capable of binding the MOI without compromising the MOI's biological activity or other desired characteristic.

In one embodiment, the MOI and the dye-type molecule are conjugated together before the dye-type molecule is dispersed into the base material.

In another embodiment, the base material may be contacted with a solution which removes impurities therein and/or thereon prior to the adhering and immobilization steps described below.

In one preferred aspect of the invention, the adhering step is carried out by dispersing the disperse dye-type molecules into an interstitial region of the base material. This is accomplished by contacting the base material with the dye-type molecule for a time sufficient to allow the dye-type molecule to disperse into the base material.

In another embodiment, the adhering step includes contacting the disperse dye-type molecule with a cross-linking reagent for a time sufficient to allow said cross-linking reagent to bind the reactive group on said dye-type molecule. The base material is then treated with the cross-linked dye-type molecule for a time sufficient to allow at least a portion of the dye-type molecule to disperse within and non-covalently adhere to said base material.

In yet another embodiment, the adhering step includes linking the dye-type molecule to a spacer molecule, such as diethyleneamine. As used herein, the term "spacer molecule" refers to a molecule, which is linked to the dye-type molecule which has a reactive group thereon to which an MOI may link. When the dye-type molecule disperses into the base material, at least a portion of the spacer molecule is available for MOI binding at the material surface. The base material is treated with the spacer-linked dye-type molecule for a time sufficient to allow the dye-type molecule to disperse into the base material. This results in the reactive group of the spacer molecule being available at the surface of the base material for linkage to a molecule-of-interest.

The immobilization step may be carried out by initially contacting the MOI with at least one molecule of a cross-linking reagent, such as a bifunctional cross-linking reagent, for a time sufficient to allow linkage of the reagent to the MOI, and then binding the MOI-linked reagent to the disperse dye-type molecule. The bound MOI retains its desired biological activity or other properties.

A bifunctional cross-linking reagent useful for such an immobilization step may be one that is heterobifunctional (e.g., N-succinimidyl 3-(2-pyridyldithio)propionate (SPDP)), homobifunctional (e.g., ethylene glycolbis (succinimidylsuccinate), (EGS)), or a mixture of both.

The term "bifunctional cross-linking reagent" is defined herein as a molecule having the ability to bind to, and therefore link, two reactive groups on, for example, one molecule or two separate molecules. If the bifunctional cross-linking reagent binds two different types of groups, it is a "heterobifunctional" cross-linking reagent. However, if the bifunctional cross-linking reagent binds only to two similar groups, it is "homobifunctional".

Prior to the binding step, the MOI may be subjected to various chromatographic procedures to remove impurities mixed in with it.

In an alternative aspect of the invention, the disperse dye-type molecule dispersed within and adhered to the base material may be linked before or after adherence to at least one molecule of a bifunctional cross-linking reagent. In this embodiment, the method further includes binding the MOI-linked reagent to the disperse dye-type molecule-linked reagent, thereby linking the MOI to the material-adhered disperse dye-type molecule.

Alternatively, the disperse dye-type molecule is linked to the MOI before it is adhered to the base material.

In yet another aspect of the invention, the disperse dye-type molecule-linked reagent is reduced prior to the binding step. The resulting exposed sulfhydryl group is then contacted with the MOI-linked reagent. Reduction results in the formation of sulfhydryl groups on the disperse dye-type molecule which can react with the MOI-linked, bifunctional cross-linking reagent via a substitution reaction to form a disulfide bond, thereby covalently linking the MOI to the disperse dye-type molecule.

The invention will next be described in connection with certain illustrated embodiments. However, it should be clear that various modifications, additions, and deletions can be made without departing from the spirit or scope of the invention.

BRIEF DESCRIPTION OF THE DRAWING

The foregoing and other objects of the present invention, the various features thereof, as well as the inventions thereof may be more fully understood from the following description when read together with the accompanying drawings in which:

FIG. 1A is Disperse Blue 1 (DB1), an anthraquinone dye; FIG. 1B is Disperse Blue 11, a monoazo dye; FIG. 1C is ciprofloxacin, a quinolone antibiotic; and FIG. 1D is alizarine, a chelating dye;

FIG. 2A shows the dispersion of a dye into the material, followed by the adherence of an MOI to a reactive group on the dye; FIG. 2B shows the dispersion of a dye with a spacer molecule into the base material such that the reactive group is at the surface of the material. The MOI (or cross-linked MOI) is then bound to the reactive group; FIG. 2C shows the dispersion of a disperse dye-type molecule into the base material and then the adherence of a cross-linked MOI to a reactive group in the disperse dye-type molecule; FIG. 2D demonstrates the adherence of a MOI-cross-linked disperse dye-type molecule directly to the base material.

FIG. 4A-D are spectrophotometric scans of HPLC chromatographs in which FIG. 4A shows DB1, alone; FIG. 4B shows BSA-SH, alone; FIG. 4C shows DB1+BSA-SH; and FIG. 4D shows DB1-SPDP+BSA-SH; and FIG. 5 is a photographic representation of a mobile phase thin layer chromatogram showing in lane 1, DB1; in lane 2, DB1+DB1-ciprofloxacin conjugate; lane 3, DB1-ciprofloxacin conjugate; lane 4, DB1-ciprofloxacin conjugate+DB1; lane 5, ciprofloxacin; and lane 6, ciprofloxacin+carbodiimide (EDC).

DESCRIPTION OF THE INVENTION

This invention provides methods of fabricating materials to which an MOI has been stably adhered. The method takes advantage of the discovery that dye-type molecules can be used as an anchor to link MOIs to various materials via reactive groups on the dye that can bind directly or indirectly to a reactive group on the MOI.

One example of useful dye-type molecule is a disperse dye-type molecule. A disperse dye-type molecule is a compound that can be absorbed into a fibrous material in a more or less permanent state with no actual chemical reaction occurring between base material and dye. With a fibrous hose material such molecules may be initially absorbed into a fibrous material and then dissolved or diffused into the fibers, themselves.

Disperse dyes, formerly called acetate dyes, were originally developed for acetate fibers. Colors found in this type of dye are primarily in the orange, red, and blue hues. These dyes are the only practical means of colorizing acetate, polyester, and triacetate fibers, and can also be applied to acrylic, aramid, monacrylic, nylon, olefin, polyester, and saran fibers. Disperse dyes fall into two categories: azo-compounds that are mainly monoazo such as Disperse Blue 11, or diazo such as Disperse Orange 15, and anthraquinone dyes such as Disperse Blue 1 and related structures (*Kirk-Othmer Encyclopedia of Chem. Tech.*, 3rd Ed. (1978-1984) (Grayson et al., eds.) Wiley Publishers, New York), 9, 19, 29, Disperse Violet 1 4, 8, Disperse Red 4, 11, 15, 60, Disperse Orange 11, 15 (Chemical Index Number CI #26080) and alizarine, a chelating dye.

Disperse dye-type molecules also encompass antibiotics that diffuse into a base material surface, thus providing functional groups for attachment of the MOIs. These antibiotics include quinolones having a chemical structure similar to the structure of anthraquinones. When affixed to a base material in accordance with the invention, such antibiotics are also useful for providing characteristics such as infection resistance to the base material.

Figure 1A:
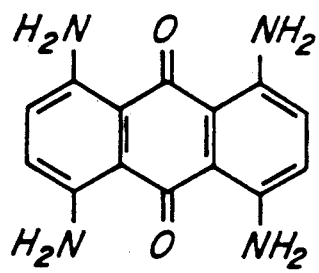
FIG. 1A-1D are schematic representations of the molecular configurations of preferable disperse dye-type molecules of the present invention.
Figure 1B:
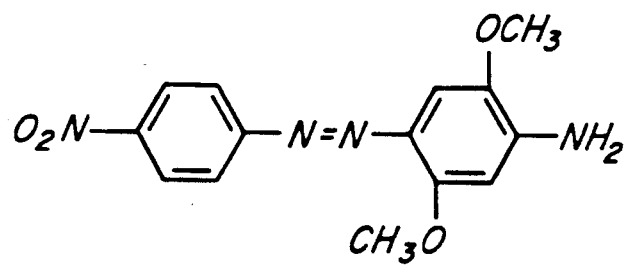
Figure 1C:
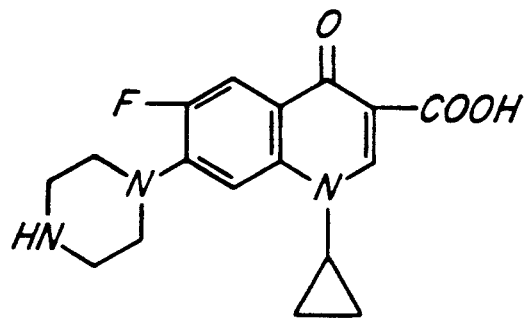
Figure 1D:
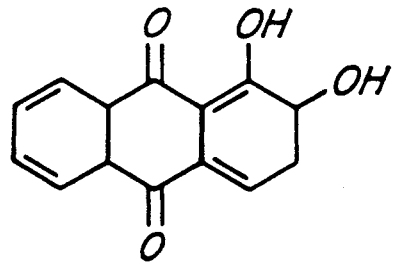

Ciprofloxacin is one example of a quinolone antibiotic (Wood (1988) British J. Clin. Prac. 42:469-472). The structure of ciprofloxacin is shown in FIG. 1C. The fluorine atom at position 6 gives the molecule improved potency against Gram-negative bacteria and broadens the spectrum to include Gram-positive organisms, while the piperazine ring at position 7 is responsible for the anti-pseudomonas activity.

Ciprofloxacin has antibacterial activity largely as a result of its ability to inhibit the action of an enzyme that acts on bacterial DNA. The in vitro spectrum of activity of ciprofloxacin is very broad. It is bactericidal at concentrations below 0.25 mg/I against almost all Enterobacteriaceae (except a minority of Enterobacter and Acinetobacter species and *Providencia stuartii*), and 90 per cent of *Pseudomonas aeruoinosa* are inhibited by less than 1 mg/I. *Haemophilus influenzae, Branhamella catarrhalis,* and *Neisseria species* are also very sensitive to ciprofloxacin.

Other useful dyes having antimicrobial and disinfective activities include gentian violet (N-[4-[Bis[4-(dimethylamino)-phenyl]methylene]-2,5-cyclohexadien-1-ylidene]-N-methyl-methaninium chloride) and methylene blue (3,7-bis(dimethylamino) phenothiazin-5-chloride).

In addition, other dyes having abilities to penetrate materials and to provide an anchoring property are also useful. These include substantive or direct dyes, azoic or naphthol dyes, acid dyes, vat dyes, and cationic or basic dyes.

The base material useful to treat according to the invention may be composed of any extrudates, woven fabrics, or unwoven fibers having enough tensile strength to withstand the rigors of whatever function the treated material has been designed to perform. In addition, if the treated material is to be a part of a device in contact with body fluids or tissues, it is preferable that the base material be biocompatible.

Synthetic materials contemplated by the instant invention are preferably polymers such as polyethylene terphthalate, nylon, polyurethane, polytetrafluoroethylene, polyglycolic acid, and mixtures thereof, the most preferred polymeric material being polyethylene terphthalate. Other synthetic fibrous materials such as acetate, triacetate, acrylic, aramid, monacrylic, olefin, polyester, and saran are also useful. Natural base materials include collagen-containing materials, and in particular, cross-linked collagen.

The base material, when obtained, may be coated with or contain various non-covalently adhered impurities whose removal may be prerequisite for the adherence of disperse dye-type molecules thereto. For example, lubricants on commercial quality polyethylene terphthalate can be removed by contacting the polyethylene terphthalate with a solution containing, for example, various detergents, solvents, or salts, which loosen and/or solubilize these impurities.

The base material may be cut before treatment to any dimensions suitable for the purpose for which it is being used. For example, it may be an integral part of an implanted heart valve or of an extracorporeal device used for hemodialysis or cardiopulmonary by-pass surgery, or it may be used to coat catheters or to line the interior of a vascular graft. Alternatively, the material may be cut to the desired dimensions after treatment.

Figure 2A:
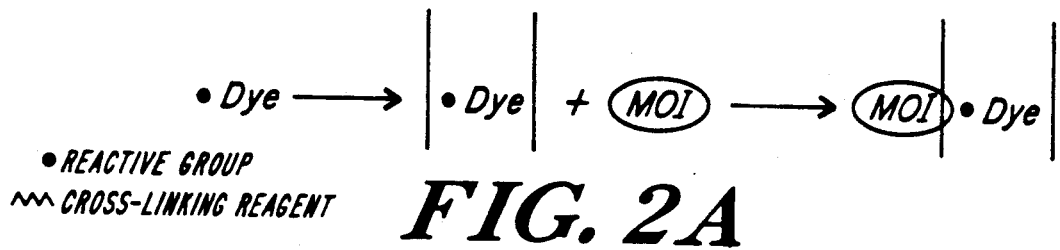
FIGS. 2A-2D are diagrammatic representations of the methods of preparing the treated material.
Figure 2B:
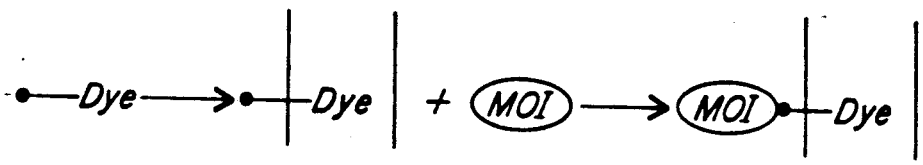

As shown in FIG. 2A, the treated material can be fabricated by dispersing the dye-type molecule into the base material, and then linking an MOI to the material via the reactive group on the dye-type molecule. In some instances, the MOI may be cross-linked to a bifunctional cross-linking reagent such as SPDP before it is linked to the dye via its reactive group FIG. 2B). In this case it is the cross-linking reagent which interacts with the reactive group.

Figure 2C:
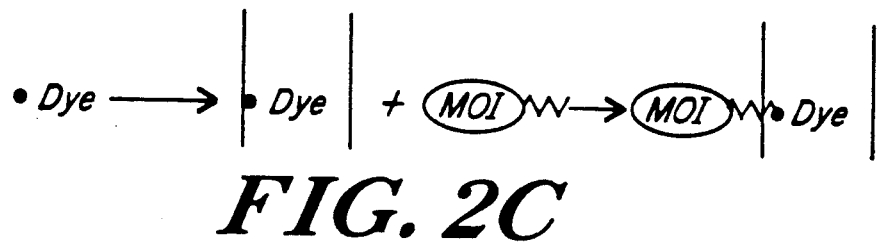

Alternatively, a reactive group on the dye-type molecule can be cross-linked to the MOI before the dye is dispersed into the base material (FIG. 2C). The material is then treated with this cross-linked dye-MOI complex, resulting in a configuration that enables the dye to penetrate the material, while allowing the MOI to be exposed on the material surface.

Figure 2D:
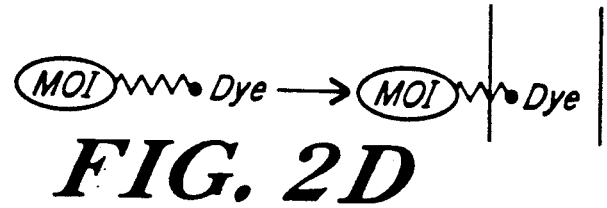
Figure 2E:
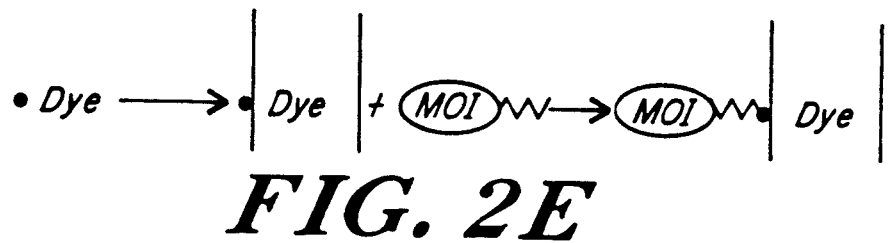
FIG. 2E shows the dispersion of a dye into the base material such that its reactive group is at the surface of the base material, followed by adherence of a cross-linked MOI to that surface-exposed reactive group.

In the embodiment shown in FIG. 2D, a spacer molecule is linked to the dye-type molecule before its dispersion into the base material. Spacers (e.g., diethylamine) can be used to enhance penetration of the dye and surface exposure of the MOI. The reactive group of these spacers remains at or extended from the surface of the dye-linked base material.

The dye-type molecule itself can be modified such that it has an extended chain that remains surface-oriented and a functional group readily available to bind cross-linking reagents or MOIs. In addition, metals such as silver or magnesium may be used to enhance the penetration of a disperse-type dye such as ciprofloxacin.

TABLES 1–5 outline representative methods of preparing the treated material, where "Da" refers to a synthetic base material composed of woven polyethylene terphthalate fibers, "MOI" refers to a molecule-of-interest, SPDP refers to the heterobifunctional cross-linking reagent N-succinimidyl 3-(2-pyridyldithio) propionate, and "P-2-T" refers to pyridine-2-thione.

TABLE 1

| STEP # | PROCESS |
|---|---|
| 1) | Da + dye → Da-dye |
| 2) | Da-dye + MOI → Da-dye-MOI |

TABLE 2

| STEP # | PROCESS |
|---|---|
| 1) | MOI + dye → MOI-dye |
| 2) | MOI-dye + Da → MOI-dye-Da |

TABLE 3

| STEP # | PROCESS |
|---|---|
| 1) | Da + dye → Da-dye |
| 2) | Da-dye + SPDP → Da-dye-SPDP |
| 3) | Da-dye-SPDP + DTT → Da-dye-SH + P-2-T |
| 4) | MOI + SPDP → MOI-SPDP |
| 5) | Da-dye-SH + MOI-SPDP → Da-dye-S-S-MOI + P-2-T |

TABLE 4

| STEP # | PROCESS |
|---|---|
| 1) | dye + SPDP → dye-SPDP |
| 2) | dye-SPDP + DTT → dye-SH + P-2-T |
| 3) | MOI + SPDP → MOI-SPDP |
| 4) | dye-SH + MOI-SPDP → dye-S-S-MOI + P-2-T |
| 5) | Da + dye-S-S-MOI → Da-dye-S-S-MOI |

TABLE 5

| STEP # | PROCESS |
|---|---|
| 1) | dye + SPDP → dye-SPDP |
| 2) | dye-SPDP + DTT → dye-SH + P-2-T |
| 3) | dye-SH + Da    Da-dye-SH |
| 4) | MOI + SPDP → MOI-SPDP |
| 5) | Da-dye-SH + MOI-SPDP → Da-dye-S-S-MOI + P-2-T |

Likewise, TABLES 6 and 7 outline exemplary methods of preparing the soluble, pharmacological cross-linking reagent, wherein "SMCC" refers to "succinimidyl 4-(N-maleimidomethyl)-cyclohexane-1-carboxylate."

TABLE 6

| STEP # | PROCESS |
|---|---|
| 1) | HSA + Traunt's → HSA-SH |
| 2) | MOI + SMCC → MOI-SMCC |
| 3) | HSA-SH + MOI-SMCC → MOI-SMCC-HSA |

TABLE 7

| STEP # | PROCESS |
|---|---|
| 1) | MOI + Traut's → MOI-SH |
| 2) | dye + SMCC → dye-SMCC |
| 3) | MOI-SH + dye-SMCC → MOI-SMCC-dye |

At least one surface of the base material is treated with a disperse dye-type molecule or dye-MOI conjugate. The dye provides reactive groups for attachment of an MOI. Such reactive groups provide more binding sites for the MOI than does the synthetic material, alone, thereby amplifying the amount of MOI which may be bound. Useful reactive groups include sulfhydryl, amino, carboxyl, aldehyde, and ketone groups, and carbon-hydrogen bonds.

Of course, the MOI may be cross-linked to a second MOI to enhance the biologic or other activities of the dye-MOI conjugate. This second MOI may be different from or the same as the first MOI.

The MOI is directly or indirectly immobilized to the disperse dye-type molecule via the use of a bifunctional cross-linking reagent. In particular, a heterobifunctional cross-linking reagent which has two different reactive groups at each end of a linear molecule, and can therefore bind two different reactive groups on other molecules or on a different region of the same molecule, is most useful as a bifunctional cross-linking reagent. For example, photoreactive cross-linkers, such as sulfosuccinimidyl 2-(m-azodo-o-nitro-benzamido)-ethyl-1, 3'-dithio-propionate (SAND), or N-succinimidyl-6-(4-azoido-2'-nitrophenyl-amino) hexanoate (SANPAH) have a photoreactive group that can directly insert into C—H bonds of the base coat by photochemical coupling, while the other group remains free to bind to proteins. Other useful and preferable cross-linking reagents such as N-succinimidyl 3-(2-pyridyldithio) propionate (SPDP) and succinimidyl 4-(N-maleimido methyl)-cyclohexane-1-carboxylate (SMCC) and their characteristics are found in TABLE 8. The "Double-Agent Number" listed for each reagent is the commercial designation for the reagent as made available by Pierce Chemical Co. (Rockford, Ill.). However, these reagents may be obtained from other commercial sources, as well.

TABLE 8

CROSS-LINKING REAGENTS (part A)

| Double-Agent Number | Double-Agent Acronym | Bifunctionality Homo | Bifunctionality Hetero | Reactive towards: NH₂ | Reactive towards: SH | Photo-Reactive |
|---|---|---|---|---|---|---|
| 21551 | ANB-NOS | | X | X | | X |
| 20106 | APB | | X | | X | X |
| 20107 | APG | | X | | | X |
| 21559 | APTP | | X | | X | X |
| 21579 | BS³ | X | | X | | |
| 22319 | BMH | X | | | X | |
| 21554 | BSOCOES | X | | X | | |
| 21524 | DFDNB | X | | X | | |
| 20047 | DIDS | X | | X | | |
| 20664 | DMA | X | | X | | |
| 20666 | DMP | X | | X | | |
| 20668 | DMS | X | | X | | |
| 22585 | DSP | X | | X | | |
| 21555 | DSS | X | | X | | |
| 20590 | DST | X | | X | | |
| 20665 | DTBP | X | | X | | |
| 22590 | DTBPA | X | | | | X |
| 21577 | DTSSP | X | | X | | |
| 21550 | EADB | | X | X | | X |
| 21565 | EGS | X | | X | | |
| 23700 | FNPA | | X | X | | X |
| 21560 | HSAB | | X | X | | X |
| 26095 | MABI | | X | X | | X |
| 22310 | MBS | | X | X | X | |
| 27715 | NHS-ASA | | X | X | | X |
| 20669 | PNP-DTP | | X | X | | X |
| 21552 | SADP | | X | X | | X |
| 21549 | SAND | | X | X | | X |
| 22588 | SANPAH | | X | X | | X |
| 27716 | SASD | | X | X | | X |
| 22325 | SIAB | | X | X | X | X |
| 22320 | SMCC | | X | X | X | |
| 22315 | SMPB | | X | X | X | |
| 21557 | SPDP | | X | X | X | |
| 21556 | Sulfo-BSOCOES | X | | X | | |
| 20591 | Sulfo-DST | X | | X | | |
| 21556 | Sulfo-EGS | X | | X | | |
| 22312 | Sulfo-MBS | | X | X | X | |
| 21553 | Sulfo-SADP | | X | X | | X |
| 22589 | Sulfo-SANPAH | | X | X | | X |
| 22327 | Sulfo-SIAB | | X | X | X | |
| 22322 | Sulfo-SMCC | | X | X | X | |
| 22317 | Sulfo-SMPB | | X | X | X | |
| 26101 | TRAUNT'S | X | | X | | |

CROSS-LINKING REAGENTS (part B)

| Agent Acronym | Chemical Name |
|---|---|
| ANB-NOS | N-5-azido-2-nitrobenzoyloxysuccinimide |
| APB | p-azidophenacyl bromide |
| APG | p-azidophenyl glyoxal |
| APTP | n-4-(azidophenylthio)phthalimide |
| BS3 | bis(sulfosuccinimidyl) suberate |
| BMH | bis maleimidohexane |
| BSOCOES | bis[2-(succinimidooxycarbonyloxy)-ethyl]sulfone |
| DFDNB | 1,5-difluoro-2,4-dinitrobenzene |
| DIDS | 4,4'-diisothiocyano-2,2'-disulfonic acid stilbene |
| DMA | dimethyl adipimidate-2 HCl |
| DMP | dimethyl pimelimidate-2 HCl |
| DMS | dimethyl suberimidate-2 HCl |
| DSP | dithiobis(succinimidylpropionate) |
| DSS | disuccinimidyl suberate |
| DST | disuccinimidyl tartarate |
| DTBP | dimethyl 3,3'-dithiobispropionimidate-2-HCl |
| DTBPA | 4,4'-diothiobisphenylazide |
| DTSSP | 3,3-dithiobis(sulfosuccinimidyl-propionate) |
| EADB | ethyl-4-azidophenyl 1,4-dithio-butyrimidate |
| EGS | ete glycolbis(succinimidyl-succinate) |
| FNPA | 1-azido-4-fluoro-3-nitobenzene |
| HSAB | N-hydroxysuccinimidyl-4-azidobenzoate |
| MABI | methyl-4-azidobenzoimidate |
| MBS | m-maleimidobenzoyl-N-hydroxysulfo-succinimide ester |
| NHS-ASA | N-hydroxysuccinimidyl-4-azidosalicylic acid |
| PNP-DTP | p-nitrophenyl-2-diazo-3,3,3-trifluoro-propionate |
| SADP | N-succinimidyl(4-axidophenyl)-1,3'-dithiopropionate |
| SAND | sulfosuccinimidyl 2-(m-azido-o-nitro-benzamido)-ethyl-1,3'-dithiopropionate |
| SANPAH | N-succinimidyl-6(4'-azido-2'-nitro-phenyl-amino)hexanoate |
| SASD | sulfosuccinimidyl 2-(p-azidosalicyl-amido)ethyl-1,3'-dithio-propionate |
| SIAB | N-succinimidyl(4-iodoacetyl)amino-benzoate |
| SMCC | succinimidyl 4-(N-maleimidomethyl)-cyclohexane-1-carboxylate |
| SMPB | succinimidyl 4-(p-maleimidophenyl)-butyrate |
| SPDP | N-succinimidyl 3-(2-pyridyldithio) propionate |
| Sulfo-BSOCOES | bis[2-(sulfosuccinimidooxy-carbonyl-oxy)ethyl]sulfone |
| Sulfo-DST | disulfosuccinimidyl tartarate |
| Sulfo-EGS | ethylene glycolbis(sulfosuccinimidyl-succinate) |
| Sulfo MBS | m-maleimidobenzoyl-N-hydro-xysulfo-succinimide ester |
| Sulfo-SADP | sulfosuccinimidyl(4-azidophenyldithio)-propionate |
| Sulfo- | sulfosuccinimidyl 6-(4'azido-2'-nithro- |

TABLE 8-continued

| | |
|---|---|
| SANPAH | phenylamino)hexanoate |
| Sulfo-SIAB | sulfosuccinimidyl(4-iodoacetyl)aminobenzoate |
| Sulfo-SMCC | sulfosuccinimidyl 4-(N-maleimidomethyl)cyclohexane-1-carboxylate |
| Sulfo-SMPB | sulfosuccinimidyl 4-(p-maleimidophenyl)butyrate |
| TRAUNT'S | 2-iminothiolane-HCl |

The cross-linking reagent may be applied to the dye-type molecule in amounts such that the desired binding site density is achieved. Binding site density is that amount of cross-linking reagent, in terms of moles/gram synthetic material, that binds to the material while providing confluent coverage of the surface.

To put the MOI in condition for linkage to the disperse dye-type molecule, the cross-linking reagent may be initially coupled separately to both the disperse dye-type molecule and to the inhibitor. The kinetic constants of the inhibitors are compared before and after coupling to evaluate effects of the procedure on their kinetic constants. The MOI should retain its biological or other activity after being coupled. Therefore, standard activity assays specific for the MOI to be immobilized are performed using a standard MOI solution to evaluate this capacity.

As an alternative, the reactive group of the disperse dye-type molecule may be first bound to the MOI forming a conjugate prior to adherence of the dye to the base material, and then the conjugate may be bound to the base material as shown in TABLE 2.

In the special case of SPDP derivatization, linkage of certain groups on the MOI to SPDP may destroy some biological activity because at least some of these groups may be required for such activity. However, by adjusting the reaction ratio of MOI to SPDP, and running the reaction at near physiological PH, SPDP becomes somewhat selective for epsilon amino groups. The result of these conditions favor a 1:1 (mole:mole) conjugation ratio of MOI to SPDP covalently bound without destroying biological activity.

SPDP will react with terminal as well as epsilon amino groups. Since derivatization of a terminal amino group can inactivate a biologically active protein, T-BLOCK (Pierce Chemical Co., Rockford, Ill.) may be used to block that group during SPDP-derivatization. The T-BLOCK is then removed after derivatization to restore biological activity.

Of course, the linkage of some dyes to some MOIs may not require the aid of a cross-linking reagent since they already possess reactive groups useful for linkage. The adherence of such dyes or dye-MOI conjugates is shown below in TABLES 3 and 4.

The invention will be further understood from the following, non-limiting examples.

EXAMPLE 1

Pretreatment of Woven Synthetic Material

Polyethylene terphthalate (PT, DuPont) is sectioned into 1.0 cm lengths. The lubricant on and in the woven surface is removed by washing once for 1 hr with carbon tetrachloride, and twice with 100% methanol ($CH_3OH$). The methanol is removed by multiple water washes, followed by one wash in phosphate buffered saline (PBS), pH 7.4.

EXAMPLE 2

Dye Application

A. Linkage of DB1 to PT

Disperse Blue 1 (DB1) (CAS Registry Number 2475-45-8, Sigma or Aldrich) is applied to the lumen of PT fabric as follows. DB1 is dissolved in 2 ml ethanol, then diluted with 98 ml distilled water. The fabric is removed and washed in PBS to remove nonspecifically bound dye. Approximately 2% or 20 mg DB1/9 g PT is dyed into the fabric.

B. Linkage of SPDP to DB-PT

The dye-bound PT material is incubated in a 1.0 mM solution of SPDP in PBS, pH 7.4, to bind SPDP to the dye (100 mM SPDP/$cm^2$ dye). Incubation is terminated after 30-40 min at room temperature (RT). The fabric is washed in PBS to remove nonspecifically bound SPDP.

C. Activation of SPDP on the DB1 and Measurement of Binding Site Density

The SPDP-linked material is dried and weighed to obtain its absolute weight. It is then placed in a 50 mM solution of dithiotreitol (DTT) for 5 min at room temperature. This reaction releases P-2-T from the bound SPDP, and simultaneously forms free sulfhydryl (SH) groups on the dye. The released P-2-T is quantitated by absorption spectrophotometry at 343 nm using its extinction coefficient ($E = 8.08 \times 10^3$), and is directly proportional to the quantity of bound SPDP or binding sites. The number of binding sites are calculated and expressed as moles of sites/g of PT.

D. Linkage of SPDP to DB1

A 104 mM DB1 solution in 100% EtOH and a 64 mM SPDP solution in 100% EtOH were prepared and mixed. The reaction mixture was incubated overnight at room temperature. The mixture was then purified by normal phase thin layer chromatography (NPTLC) using a mobile phase of 1:1 mixture of ethyl acetate:toluene. The purified band (on silica) was scraped from the TLC plate and eluted from the silica with 100% EtOH. The silica/DB1 solution was spun at 13 for 14 minutes on a table top centrifuge. The silica pellet was discarded and the supernatant was decanted into a test tube. The EtOH, from the DB1-SPDP conjugate, was evaporated off almost to dryness. The remaining DB1-SPDP was reconstituted in phosphate buffered saline (PBS).

E. Linkage of Traut's Reagent to BSA

A 149 $\mu M$ bovine serum albumin (BSA) solution in PBS and a 103 mM Traut's solution in PBS were prepared and mixed. The reaction was incubated for 30 minutes at 37° C. and 30 minutes at room temperature.

F. Conjugation of DB1-SPDP to BSA-SH and Analysis

The DB1-SPDP and BSA-SH solutions were mixed together in 10:1 (mole:mole) ratios. Incubation of the mixture occurred overnight at room temperature on the inversion mixer.

Analysis of the DB1-SPDP, BSA-SH, BSA-S-SPDP, and DB1-BSA was done by gel filtration utilizing a Pharmacia Superose 12 HR column connected to Shimadzu High Performance Liquid Chromatograph (HPLC). The mobile phase used for the isocratic system was HPLC grade PBS pH 7.4. Sample injection volume was 100 $\mu l$ and absorbance was monitored at 275 nm.

The results showed an increase in absorbance for the BSA-DB1 conjugate, indicating that successful conjugation had occurred. Protein concentrations were identical, as determined by Lowry protein analysis.

G. Linkage of DB1-SPDP to PT

Woven fiber grafts of PT were dyed with DB1-SPDP to enhance BSA-SH binding 1 $cm^2$ grafts were dyed with DB1 or with DB1-SPDP. Each group was then incubated with equal amounts of BSA-SH (MOI) for identical time periods On the average, DB1 grafts bound 6.0 μg BSA-SH using DB1-SPDP dyed grafts. These tests demonstrate that DB1-SPDP-treated grafts increased binding of BSA-SH to PT graft material by 2.25-fold. These results suggest that DB1 is bound at only one of the available amino groups per molecule.

Figure 3:
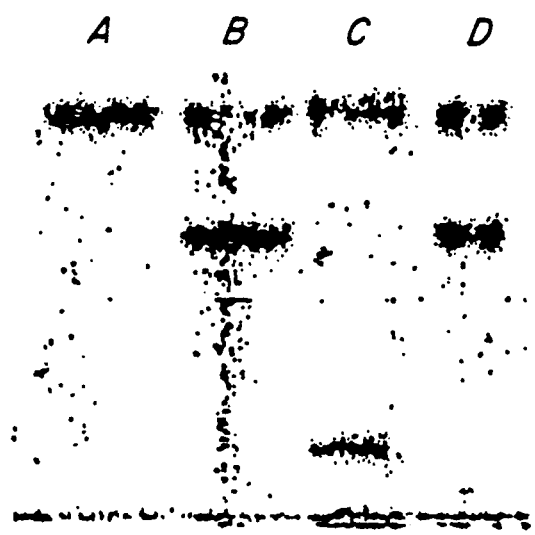
FIG. 3 is a photographic representation of a thin layer chromatography (TLC) plate demonstrating that DB1 is bound to the cross-linked SPDP at only one of the available amino groups per DB1 molecule.

This is also shown on the TLC Plate shown in FIG. 3 where DB1-SPDP shows a single derivatized band and a parent product (lanes B,C), compared to DB1 only (lane A). When DB1-SPDP is reduced with dithiothreitol (DTT), the band returns to the rf value of the parent and a P-2-T by-product band appears in the lower portion of the lane (lane C).

H. HPLC

Figure 4A:
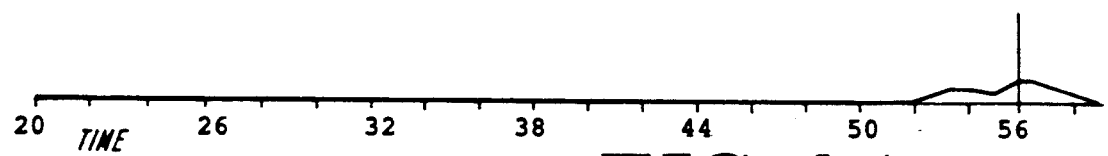
Figure 4B:
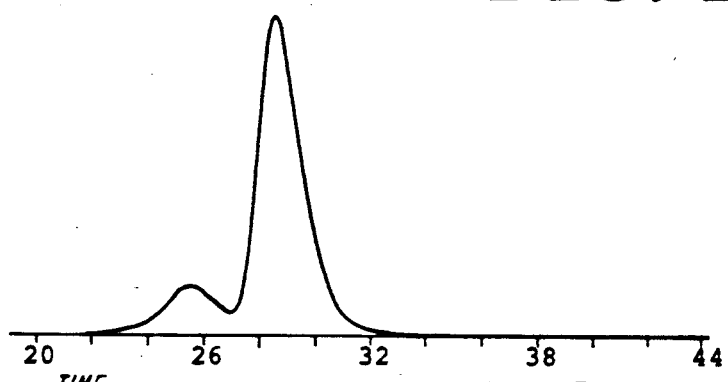
Figure 4C:
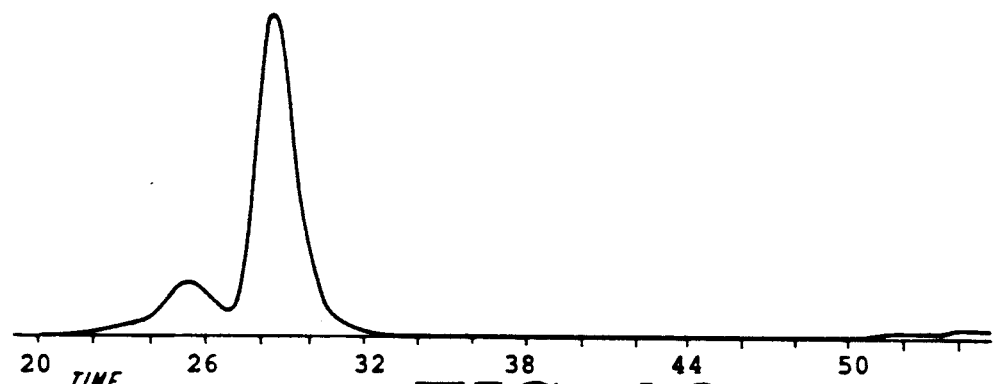
Figure 4D:
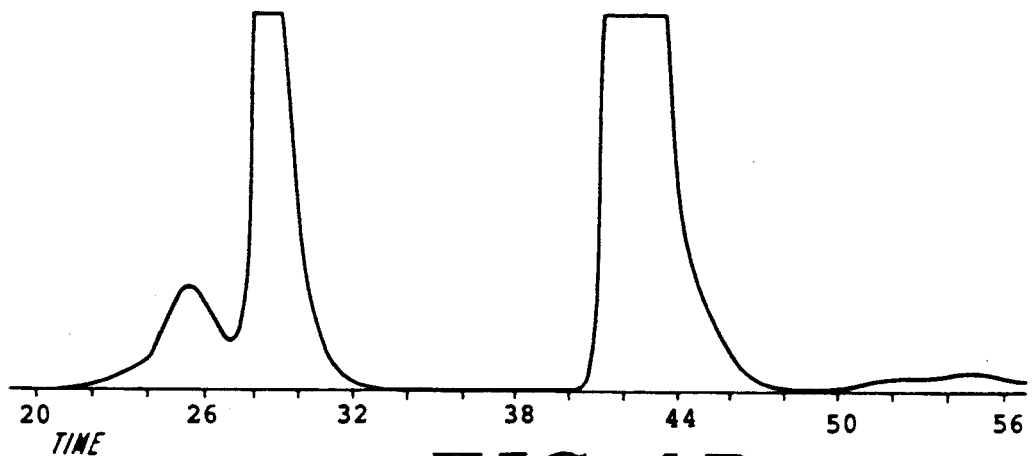

High pressure liquid chromatography (HPLC) was performed using Superose 12, molecular sieve (Pharmacia Upsaala, Sweden) in order to determine if and how much of the cross-linked SPDP covalently attached to DB1. HPLC analysis was performed as follows:

FIG. 4A shows the dye, DB1, alone without bovine serum albumin (BSA-SH, the MOI), whereas the chromatographs shown in FIG. 4B (BSA-SH), 4C (DB1+BSA-SH) and 4D (DB1-SPDP+BSA-SH) were performed with quantitatively equal amounts of BSA-SH as confirmed by Lowry protein analysis of each peak. The chromatograph shown in FIG. 4C is equal in quantity of BSA in the 28 peak as well as adsorption at $A_{280}$ as that in the chromatograph shown in FIG. 4B, suggesting no DB1 bound to BSA-SH. The chromatograph in FIG. 4D shows an increase of 49% over those in FIGS. 4B and 4C in the 28 peak; however, FIG. 4D shows an equal amount of BSA as shown in FIGS. 4B and 4C as determined by Lowry Protein analysis. This is evidence of binding of DB1-SPDP to BSA. In addition, the appearance of a large peak at position 42 is due to P-2-T, the by-product of the SPDP reaction. This is further evidence of the covalent attachment of DB1 to BSA using SPDP as the cross-linker.

EXAMPLE 3

Antibiotic Immobilization

A. Application of Ag and Mg to PT

A 47 mM solution of $AgNO_3$ in 70% EtOH/30% water and a 59 mM solution of $MgCl_2$ (same solution as above) were each added to 1 cm×1 cm PT patches. The patches in metal solutions were then heated at 100° C. for 30 minutes. After hearing, the patches were air dried in an oven at 100° C. for 15 minutes and washed in phosphate buffered saline (PBS) for time increments of 1 hour, 1 day and 2 days to determine the effectiveness of coating PT with metals.

B. Application of Ciprofloxacin with Ag and Mg to PT

Silver and magnesium were used to enhance ciprofloxacin presence on the PT surface. 1 cm×1 cm PT patches were placed into a 26 mM (Miles Lab, West Haven, Conn.) ciprofloxacin solution in 60% EtOH. 2 ml of 47 mM silver and 69 mM magnesium were added to the 26 mM ciprofloxacin with the PT present. A white suspension occurs upon addition of silver to ciprofloxacin. The patches in metal solutions were then heated at 100° C. for 30 minutes. After heating, the patches were air dried in an oven at 100° C. for 15 minutes and washed in phosphate buffered saline (PBS) for time increments of 1 hour, 1 day, and 2 days to determine the effectiveness of coating PT with metals.

C. Linkage of DB1 to Ciprofloxacin

A 35 mM DB1 solution in 100% EtOH was prepared and added to a 36 mM ciprofloxacin solution. Cross-linking occurred with addition of 75 mM carbodiimide (EDC) in 100% EtOH. Incubation was two hours at room temperature. Confirmation of product was shown by thin layer chromatography (TLC) and wavelength scanning, and by HPLC analysis.

D. Characterization of DB1-Ciprofloxacin Conjugate

The conjugate was run on mobile phase thin layer chromatography (MPTLC) using a mobile phase consisting of 1 part 100% EtOH, 4 parts n-BuOH, 2 parts pyridine, and 3 parts $NH_3OH$. The results in FIG. 5 show a new band formed (DB1-ciprofloxacin conjugate, lane 3) which undergoes fluorescence in the presence of ultraviolet light.

The conjugate was further characterized by C18 reverse phase high pressure liquid chromatography (RPHPLC). For the binary system, mobile phase A was lacetic acid, pH 5.0, and mobile phase B was 20% mobile phase A 80% acetonitrile. The gradient parameters were 0–45% B over 29 minutes and from 45% to 100% over 11 minutes. These results show formation of a more polar product than the standard runs.

A wavelength scan from 700 nm to 260 nm was also used to characterize the conjugate. The scan results show a shift in wavelength absorption by the conjugate as compared to the controls. The reaction was stopped by application of the sample to a Pharmacia PD-10 column (Sephadex G-25) which separated sulfhydryl albumin from free Traut's. The first peak fractions contained sulfhydryl albumin and were pooled.

E. Application of Alizarine to PT

A 0.5% alizarine (Aldrich, Milwaukee, Wis.) solution in water was prepared. The amount of alizarine used was based on 2% of the weighted fiber (OWF). Therefore, 3.2 ml of the 0.5% alizarine solution was transferred into 96.8 ml of 1% acetic acid, at a pH of approximately 5.0. 0.8 g of PT patches were added to the dye bath and heated at 130° C. for one hour. After dyeing, the patches were washed with distilled water and stored for later use.

F. Linkage of Ciprofloxacin and Ag to Alizarine-Treated PT

Alizarine-treated patches were placed into a 26 mM ciprofloxacin solution in 70% EtOH and a 47 mM silver solution in 70% EtOH. The dye baths were heated to 100° C. for 30 minutes. The patches in metal solutions were then heated at 100° C. for 30 minutes. After hearing, the patches were air dried in an oven at 100° C. for 15 minutes and washed in phosphate buffered saline (PBS) for time increments of 1 hour, 1 day and 2 days to determine the effectiveness of coating PT with metals.

Plating the remaining dye bath on TLC indicates the formation of a new product with alizarine and ciprofloxacin. No product is shown with silver.

EXAMPLE 4

Linkage via Pad/Heat Treatment

Ciprofloxacin amyl was prepared as follows. 10 mM ciprofloxacin was dissolved in 1.0 ml of amyl alcohol. Addition of 100 μl concentrated sulfuric acid catalyzed the reaction. Total reaction time was 6 hours at 130° C. TLC verified ciprofloxacin amyl formation.

Ciprofloxacin, ciprofloxacin-EDC, conjugate, ciprofloxacin amyl, and alizarine-ciprofloxacin were prepared as described above. An aliquot of each sample solution was spotted separately on a 12"×6" piece of PT. The PT was air dried at room temperature and heated for two minutes at 210° C. The patch cooled to room temperature and was washed three times for three minutes with a non-ionic detergent, Synthrapol S.P. (ICI, Wilmington, Del.) and distilled water. The patch was air dried at room temperature overnight. Then a 1 cm×1 cm piece of PT was cut from each dyed compound. These pieces were autoclaved for 15 minutes at 130° C.

EXAMPLE 5

Infection Resistance Activity Assay

Patches were placed into in vitro cultures of $10^5$ Staphylococcus epidermidis to determine if the compounds still contained anti-microbial properties. The patch was incubated in 1 ml of trypticase soy broth with $10^5$ S. epidermidis cells for 24 hours. If the patch had effective antibacterial activity, the broth remained clear. In control sample with no activity, the broth became turbid.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A treated material comprising:
   (a) a base material selected from the group consisting of an extrudate, an unwoven fabric, and a woven fabric, and said base material is made from at least one polymer selected from the group consisting of polyethylene terephthalate, nylon, polyurethane, polytetrafluoroethylene, polyglycolic acid, monoacetate of polyglycolic acid, triacetate of polyglycolic acid, aramid, vinylidene polymer plastics, and mixtures thereof;
   (b) a disperse dye molecule having at least a portion embedded within and non-covalently adhered to said base material, said dye molecule comprising an anthraquinone dye which has a reactive group; and
   (c) a molecule-of-interest comprising a peptide, immobilized on said base material by way of said reactive group of said dye molecule, said molecule-of-interest retaining its activity when immobilized, said treated material having the activity of said molecule-of-interest.

2. The treated material of claim 1 wherein said synthetic base material comprises polyethylene terphthalate.

3. The treated material of claim 1 wherein said reactive group of said dye is selected from the group consisting of an amino group.

4. The treated material of claim 1 wherein said disperse dye molecule is an anthraquinone dye selected from the group consisting of Disperse Blue 1, 9, 19, 29, Disperse Violet 1, 4, 8, Disperse Red 4, 11, 15, 60, and Disperse Orange 11.

5. The treated material of claim 1 wherein said molecule-of-interest is immobilized on said reactive group of said dye molecule via a cross-linking agent.

6. The treated material of claim 5 wherein said molecule-of-interest is immobilized on said reactive group of said dye molecule via a bifunctional cross-linking agent.

7. The treated material of claim 6 wherein said molecule-of-interest is immobilized on said reactive group of said dye molecule via N-succinimidyl 3-(2-pyridyldithio) propionate (SPDP).

* * * * *